United States Patent [19]

Nei et al.

[11] 4,274,280

[45] Jun. 23, 1981

[54] PLUGGING INDICATOR

[75] Inventors: Hiromichi Nei; Ryoichi Ohtani, both of Yokohama; Iwao Ohshima, Kawasaki; Yuji Horikawa, Tokyo, all of Japan

[73] Assignee: Tokyo Shibaura Denki Kabushiki Kaisha, Kanagawa, Japan

[21] Appl. No.: 79,203

[22] Filed: Sep. 26, 1979

[30] Foreign Application Priority Data

Oct. 2, 1978 [JP] Japan ............................ 53/120415

[51] Int. Cl.³ ........................................ G01N 11/00
[52] U.S. Cl. ............................................. 73/61 LM
[58] Field of Search ................ 73/61 LM, 15 R, 17 R

[56] References Cited

U.S. PATENT DOCUMENTS

| | | | |
|---|---|---|---|
| 2,997,874 | 8/1961 | Billuris et al. | 73/61 LM |
| 3,222,916 | 12/1965 | Davis | 73/61 LM X |
| 3,343,401 | 9/1967 | Delisle | 73/61 LM X |
| 3,462,997 | 8/1969 | Roach et al. | 73/61 LM |
| 3,624,709 | 11/1971 | Petrek | 73/61 LM |
| 4,178,795 | 12/1979 | Nagai | 73/61 LM |

*Primary Examiner*—Gerald Goldberg
*Assistant Examiner*—Joseph W. Roskos
*Attorney, Agent, or Firm*—Stevens, Davis, Miller & Mosher

[57] ABSTRACT

A plugging indicator comprises an economizer having concentric outer and inner pipes one ends of which are connected to a main conduit through which liquid metal passes, an electromagnetic pump mounted on the outer pipe for branching the liquid metal into the outer pipe, a device for measuring flow quantity of the liquid metal passing through the outer pipe, and cooling means mounted on the outer pipe. The inner pipe is provided with two openings as a plugging orifice and a by-pass orifice to deposit impurities contained in the liquid metal. The plugging indicator further comprises a thermometer for measuring temperature at the plugging orifice, a blower for supplying cooling air to the cooling means, and a device for controlling the blower in response to the flow quantity at the flow quantity measuring device and the temperature at the plugging orifice.

2 Claims, 4 Drawing Figures

PLUGGING INDICATOR

BACKGROUND OF THE INVENTION

This invention relates to an improvement of a plugging indicator capable of measuring concentration of impurities contained in liquid metal on the principle that impurities contained in liquid metal deposit when the concentration thereof exceeds the saturation solubility.

In a fast breeder reactor or a testing equipment utilizing sodium in which liquid sodium is utilized as a coolant, it is necessary to control or supervise the degree of purity of the sodium by taking into consideration a corrosion check, abrasion check an of a material utilized to construct the equipment, and a leakage detection of water in a steam generator used in the equipment. In order to inspect or monitor the degree of the purity of the liquid sodium, a plugging indicator is generally used.

Generally, the concentration of the impurities contained in the liquid sodium is measured by the plugging indicator wherein the liquid sodium branched from a main conduit of, for example, a testing equipment utilizing sodium into the plugging indicator is cooled to deposit the impurities at a restricted portion so as to increase the pressure drop at the restricted portion, a flow quantity of the liquid sodium is reduced by the pressure drop, and a temperature of the liquid sodium at the restricted portion is measured when the flow quantity thereof is reduced. Thus, the concentration of the impurities contained in the liquid sodium can be determined on the basis of this temperature.

FIG. 1 shows a prior art plugging indicator in which liquid sodium passing through a main conduit 1 of a piece of sodium test equipment is branched by the action of an electromagnetic pump 3 into an inlet or branch pipe 2 and then flows into an economizer or a heat exchanger 5 comprising an inner pipe 9 while the flow quantity of the liquid sodium is measured by a flow meter 4 mounted on the inlet pipe 2. The liquid sodium passing through the economizer 5 is fed through a cooler 6 to a restricted portion called a plugging orifice 7 positioned downstream the cooler 6, where a plugging temperature, i.e. temperature at this restricted portion, is measured by a thermometer 8 disposed thereat.

The liquid sodium then flows into an outlet pipe 10 through the inner pipe 9 of the economizer 5 and returns back into the main conduit 1. The plugging indicator shown in FIG. 1 further includes a by-pass pipe 11 connecting the inlet pipe 2 to the outlet pipe 10. The by-pass pipe 11 is also provided with a restricted portion 12 in connection with the plugging orifice 7.

In the plugging indicator of the type described above, although a suitable A.C. exited electromagnetic pump is used as the pump 3, since it occupies a considerably large space around the inlet pipe 2, the size of the plugging indicator is increased. In addition, in order to deposit a suitable quantity of the impurities contained in the liquid sodium at the plugging orifice 7, a large quantity of liquid sodium has to be branched into the plugging indicator for the reason that a larger quantity of liquid sodium flows into the bypass pipe 11 than that flowing through the plugging orifice 7, so that elements such as the electromagnetic pump and cooler must have a large size. Moreover, the electromagnetic pump 3, flow meter 4, thermometer etc. must be made compact or easily detachable for the purpose of inspecting, maintaining or exchanging the plugging indicator regularly once or twice a year. Particularly, it is difficult to dismount the electromagnetic pump 3 from the inlet pipe 2 without cutting the pipe in the prior art plugging indicator of the type shown in FIG. 1.

SUMMARY OF THE INVENTION

Accordingly, an object of this invention is to obviate defects described above and to provide an improved compact plugging indicator permitting easy inspection and maintenance of the elements incorporated therein and which is capable of measuring concentration of impurities of liquid metal by using a small quantity thereof.

According to this invention, there is provided a plugging indicator which comprises concentric outer and inner pipes one ends of which are connected to a main conduit through which liquid metal passes, the inner pipe being provided with a first opening at an end wall thereof remote from the main conduit to act as a plugging orifice and a second opening through the side wall thereof near the main conduit to act as a by-pass orifice, an electromagnetic pump mounted on the outer pipe for branching the liquid metal passing through the main conduit into the outer pipe, a device for measuring flow quantity of the liquid metal passing through the outer pipe, cooling means mounted on the outer pipe, a thermometer for measuring temperature at the plugging orifice, a blower for supplying cooling air to the cooling means, and a device for controlling the blower in response to the flow quantity at the flow quantity measuring device and the temperature at the plugging orifice.

BRIEF DESCRIPTION OF THE DRAWINGS

In the accompanying drawings.

DESCRIPTION OF THE PREFERRED EMBODIMENT

Figure 2:
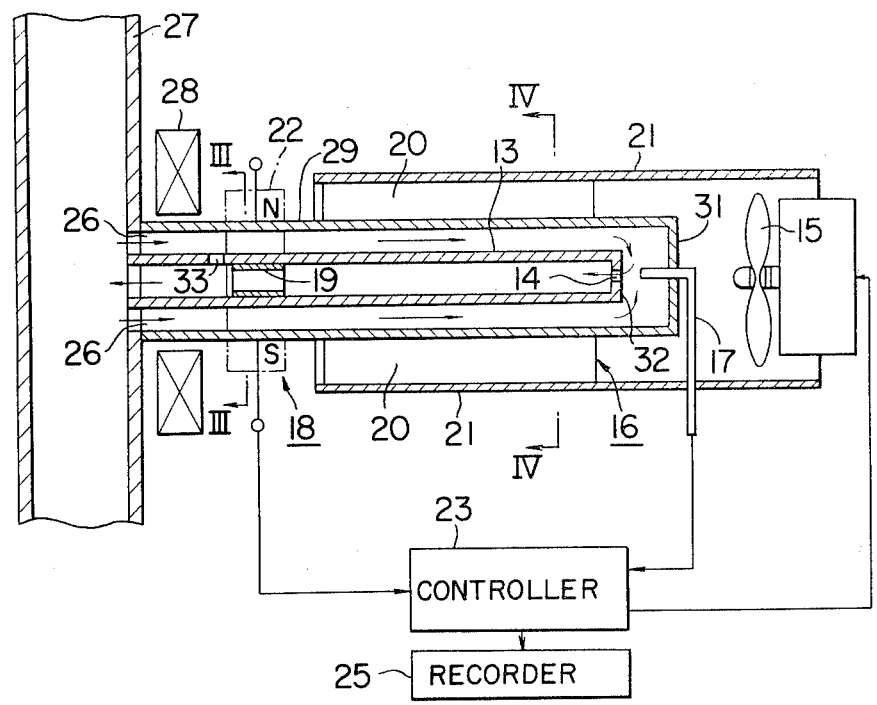
FIG. 2 is a longitudinal sectional view of a plugging indicator according to this invention.

In one example of a plugging indicator embodying the invention and shown in FIG. 2, an economizer generally comprises outer and inner pipes 29 and 13 one ends of which are connected to the side surface of the main conduit 27 of, for example, a fast breeder reactor or sodium test equipment so as to be communicated therewith.

Liquid metal such as liquid sodium passing through the main conduit 27 is branched into the space between the outer and inner pipes 29 and 13 through a passage 26 by the operation of an electromagnetic pump 28 which is mounted on the outer pipe 29 at the position near the main conduit 27. The liquid metal then collides against an end wall 31 of the outer pipe 29 and turns its flow direction towards an opening provided for the end wall 32 of the inner pipe 13 to act as a plugging orifice 14. Another opening is provided for the inner pipe 13 at the portion near the main conduit 27 to act as a bypass orifice 33 for controlling the amount of the liquid metal flowing through the plugging orifice 14.

Figure 4:
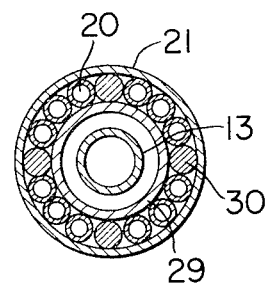
FIG. 4 is a cross-sectional view taken along the line IV—IV shown in FIG. 2.

A plurality of heat radiating members 20 which comprise a cooler 16 are mounted on the peripheral surface of the outer pipe 29 and a duct 21 is disposed to sourround the members 20. A motor driven blower 15 is attached to the end portion of the duct 21 remote from the main conduit 27, for feeding cooling air to the cooler 16 to cool the liquid metal thereby depositing impurities contained therein at the plugging orifice 14. A cross-section of a portion constructing the cooler 16 is shown in FIG. 4. A thermometer 17 is disposed at a portion suitable for measuring the temperature of the liquid metal passing through the plugging orifice 14.

Figure 1:
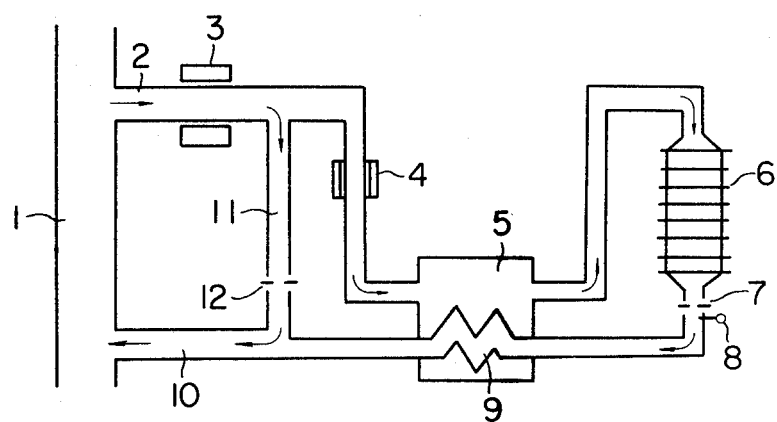
FIG. 1 is a schematic view showing a conventional plugging indicator.
Figure 3:
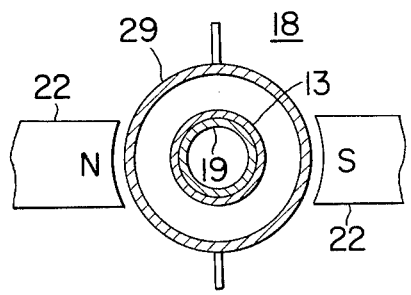
FIG. 3 is a cross-sectional view taken along the line III—III shown in FIG. 2.

A flow meter generally designated by a reference numeral 18 is located near the bypass orifice 33 and the cross-section thereof is shown in FIG. 3. The flow meter 18 comprises a permanent magnet 22 mounted on the outer pipe 29 to generate magnetic field and a magnetic shielding member 19 made of soft steel, for example, which is secured to the inner surface of the pipe 13 to shield the same from the magnetic field. Electromotive force generated by the magnetic field in the liquid metal passing through the outer pipe 29 is utilized as a flow quantity signal. Thus, since the flow meter 18 can be constructed to be compact by utilizing the magnetic shielding member, it is not necessary to arrange a flow meter about the pipe as designated by reference numeral 4 in FIG. 1 which requires additional space. Moreover, additional elements such as a preheater and a thermometer which have to be used for the flow meter of the type shown in FIG. 1 can be eliminated by providing the flow meter 18 having the structure described above.

In the cooler 16 shown in FIG. 4, the cylindrical heat radiating members 20 are secured to the outer pipe 29 by using auxiliary members such as ducts or wires, not shown, and latent heat of the liquid metal is transferred through the wall of the pipe 29 to the cooling air which passes through the spaces between the pipe 29 and the duct 21 thereby cooling the liqiud metal. The members 20 thus attached can be more easily be detached than those secured by welding as in the prior art. Because the members 20 are easily detachable, the electromagnetic pump 28 and the magnet 22 of the flow meter 18 are also easily detached at a time of inspecting or exchanging them. Several pipes 30 (in FIG. 4, four members are shown) are arranged in the heat radiating members 20 for heating or preheating the same.

Signals representing the flow quantity of the liquid metal and having a magnitude corresponding to the velocity thereof are generated by the flow meter 18 and sent to a controller 23 which acts to drive the blower 15. To the controller 23 in applied a signal generated by the thermometer 17 and showing the temperature of the liquid metal at the plugging orifice 14.

The temperature of the liquid metal at the plugging orifice 14 fluctuates around the temperature at which the impurities contained therein saturate the solution. Therefore, if the relationship between concentrations of the impurities in a given liquid metal and the temperatures at which the impurities saturate at their concentrations has been experimentally determined, then the concentration of the impurities of the liquid metal at the plugging orifice would be automatically determined by comparing the temperature at the plugging orifice with the preliminarily determined relationship described above. The concentration thus obtained is recorded by a recorder 25 connected to the controller 23.

As described hereinabove, according to this invention, there is provided a compact plugging indicator having a light weight. In addition, the plugging indicator is connected only at one portion to the main conduit of, for example, a fast breeder reactor, so worker labor in attaching the plugging indicator can be reduced. Furthermore, since elements constructing the plugging indicator such as the electromagnetic pump, flow meter, cooler etc are easily detachable, the plugging indicator can easily be inspected and maintained. Morevover, it becomes possible to operate the plugging indicator with a considerably small quantity of liquid metal, so that energy for cooling or heating the liquid metal and the elements can be reduced, thereby enabling quick measurement of the concentration of impurities contained in the liquid metal at the plugging orifice.

We claim:

1. A plugging indicator comprising concentric outer and inner pipes one ends of which are connected to a main conduit through which liquid metal passes, said inner pipe being provided with a first opening at an end wall thereof remote from said main conduit to act as a plugging orifice and a second opening through the side wall thereof near said main conduit to act as a bypass orifice, an electromagnetic pump mounted on said outer pipe for branching said liquid metal passing through said main conduit into said outer pipe, means for measuring flow quantity of the liquid metal passing through said outer pipe, cooling means mounted on said outer pipe, means for measuring temperature at said plugging orifice, a blower for supplying cooling air to said cooling means, and means for controlling said blower in response to the flow quantity at said flow quantity measuring means and the temperature at said plugging orifice.

2. The plugging indicator according to claim 1 wherein said means for measuring flow quantity of said liquid metal comprises a magnet mounted on said outer pipe to generate a magnetic field across said outer and inner pipes, and a magnetic member secured to said inner pipe to shield the interior of said inner pipe from said magnetic field, whereby an electromotive force is generated proportional to the flow quantity of the liquid metal passing through said outer pipe.

* * * * *